United States Patent [19]

Hiratsuka et al.

[11] 4,337,065

[45] Jun. 29, 1982

[54] METHOD FOR IMMUNOLOGICAL ASSAY USING MULTILAYER ANALYSIS SHEET

[75] Inventors: Nobuo Hiratsuka, Tokyo; Yuji Mihara, Minami-ashigarashi; Nobuhito Masuda, Minami-ashigarashi; Takushi Miyazako, Minami-ashigarashi, all of Japan

[73] Assignee: Fuji Photo Film Co., Ltd., Kanagawa, Japan

[21] Appl. No.: 191,784

[22] Filed: Sep. 29, 1980

[30] Foreign Application Priority Data

Sep. 27, 1979 [JP] Japan .................. 54-124514

[51] Int. Cl.³ ............... G01N 33/54; G01N 33/58; G01N 33/52
[52] U.S. Cl. ................... 23/230 B; 23/915; 422/56; 424/12
[58] Field of Search ........... 23/230 B; 422/56; 424/12

[56] References Cited

U.S. PATENT DOCUMENTS 4,168,146  9/1979  Grubb .................. 422/56

Primary Examiner—Sidney Marantz
Attorney, Agent, or Firm—Sughrue, Mion, Zinn, Macpeak and Seas

[57] ABSTRACT

In a photochemical immunological assay, an antigen or antibody is labelled with a spectral sensitizer or fogging agent for photographic use, and then an immune reaction is caused. The resulting reaction mixture is dropwise added to a multilayer analysis sheet. After either one of the labelled antigen or antibody (F) or the labelled antigen-antibody bound product (B) is brought into contact with silver halide by passing either one through a B/F separating layer provided in the multilayer analysis sheet, the analysis sheet is exposed with a light that the spectral sensitizer or fogging agent absorbs. Then, the resulting optical density obtained by development processing when a spectral sensitizer is used, or without development processing when a fogging agent is used is measured.

The multilayer analysis sheet comprises a support having provided thereon a silver halide layer and a B/F separating layer and makes the photochemical immunological assay simpler and more accurate.

9 Claims, 1 Drawing Figure

METHOD FOR IMMUNOLOGICAL ASSAY USING MULTILAYER ANALYSIS SHEET

BACKGROUND OF THE INVENTION

1. Field of the Invention

This invention relates to a method for immunological assay of immunologically active substances in vitro using a multilayer analysis sheet. More particularly, this invention relates to a method for immunological assay using a multilayer analysis sheet comprising a support having provided thereon (1) a silver halide photosensitive layer and (2) a layer capable of separating an antigen or antibody from an antigen-antibody bound product, a so-called B/F separating layer, in which silver halide is utilized in detecting such immunologically active substances. In this invention, this particular method is tentatively termed "photochemical immunological assay".

2. Brief Description of the Prior Art

Since Berson and Yalow succeeded in determining insulin in blood serum using bovine insulin labelled with radioactive iodine and anti-insulin antibody found in serum of a patient with diabetes in 1958, radioimmunoassay (referred to as "RIA") has widely been used. However, various shortcomings are encountered with RIA because radioactive substances are used. For this reason, attention has recently been brought to assays in which a radioisotope labelling is replaced by other labellings. Thus, enzyme immunoassay, fluorescent immunoassay and the like have been proposed, in which enzyme, fluorescent substances, etc. are used, respectively, as labelling substances.

RIA, enzyme immunoassay, fluorescent immunoassay, etc., however, involve disadvantages, on the other hand, that a centrifugal separator should be used upon B/F separation, time required for assay is prolonged and procedures become complicated. For example, the following methods for B/F separation are established in RIA, i.e., a paper filter method (R. S. Yalow and S. A. Berson, *J. Clin. Invest.*, 39, 1157 (1960)), a two antibody method (C. R. Morgan and A. Lazarow, *Diabetes*, 12, 115 (1963)), a salting-out method (G. Grodsky and P. H. Forsham, *J. Clin. Invest.*, 39, 1070 (1960)), an ethanol precipitation method (Nakamura et al.: *TONYOBYO (DIABETES)*, 15, 18 (1972)), a polyethylene glycol method (Nakagawa et al., *TONYOBYO (DIABETES)*, 15, 403 (1972)), a dextran carbon powder method (V. Herbert et al., *J. Clin. Endocr.*, 25, 1375 (1965)), a resin method (F. Melani et al., *Klin. Wschr.*, 43, 1000 (1965)), a talc method (G. Rosselin et al., *NATURE* 212, 355 (1966)), a Sephadex method (Ide, *RINSHO SEIJINBYO*, 2, 87 (1972)), etc. Any of these methods possesses both advantages and disadvantages.

However, RIA is subject to several disadvantages due to the use of radioactive isotopes. Thus, RIA involves the danger of radiation exposure and it is necessary to manage expensive and unstable isotopes which can result in reduced accuracy of assay. In addition, special installations, equipment and personnel qualified to deal with radiation are required. Finally, after RIA, disposal of radioactive waste material and the ensuing pollution problems are encountered.

Thus, the photochemical immunological assay has previously been proposed, details of which are disclosed in our co-pending applications Ser. Nos. 126,919 and 126,920, both filed Mar. 3, 1980.

SUMMARY OF THE INVENTION

Therefore, an object of this invention is to provide an improved method for photochemical immunological assay without any radiation danger which is simple to operate and always provides high reproducibility.

The above object has been attained by providing a multilayer analysis sheet, in the photochemical immunological assay method, which comprises a support having provided thereon a silver halide layer and further thereon a B/F separating layer. These layers can be composed of a single layer, respectively, or of a plurality of layers, if necessary. Here, the term "B/F separating layer" is used to refer to a layer for separating a labelled antigen or antibody (F) from a labelled antigen-antibody bound product (B).

DETAILED DESCRIPTION OF THE INVENTION

Figure 1:
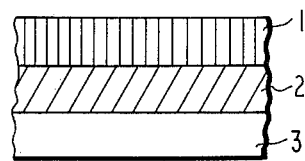
FIG. 1 is a cross-sectional view of a typical example of the multilayer analysis sheet employed in the method of this invention wherein numeral 1 represents a B/F separating layer, numeral 2 represents a silver halide layer and numeral 3 represents a support.

More specifically, in the photochemical immunological detection and assay for a trace component(s) present in solution (e.g., whole blood, blood serum, urine, etc.), the method comprises labelling an antigen or antibody with a spectral sensitizer for photographic use, i.e., an organic dye having an absorption region longer than intrinsic absorption wavelength region of silver halide, preferably longer than 500 nm, and then causing an immune reaction, the resulting reaction mixture is dropwise added to the multilayer analysis sheet. After a fixed period of time has lapsed (More specifically, the following change would occur in the analysis sheet: spotting→swelling→intake of the labelled substance (B or F) depending upon the type of separation described hereinafter→adsorption of the labelled substance (B or F) onto silver halide grains), the analysis sheet is exposed to light that the spectral sensitizer absorbs from the side of the support, from the side of the B/F separating layer or from the side of the emulsion layer after the B/F separating layer is stripped off. Thereafter, the analysis sheet is developed in a conventional manner in the photographic art. The so obtained optical density of the analysis sheet is measured to determine an unknown amount of an antigen or antibody. Separately, a known amount of labelled antigen or labelled antibody is reacted with an antigen or antibody. After separating, one of the labelled substances is quantitatively assayed using the analysis sheet of this invention to prepare a calibration curve. Based on the so obtained calibration curve, an unknown amount of an antigen or antibody can be determined.

The photochemical immunological assay using the multilayer analysis sheet of this invention can also be performed by the following method: that is, an immune reaction is caused using an antigen or antibody labelled with a fogging agent for silver halide, instead of a spectral sensitizer for photographic use, and after adding the reaction mixture dropwise onto the analysis sheet, development is performed and the so obtained density is measured. As is clear from its purpose, so called "exposure" is not necessary. Details of this method are described in Ser. No. 126,919 filed Mar. 3, 1980.

The amount of the reacton mixture dropwise added to the multilayer analysis sheet is not overly limited; from a practical standpoint, however, it should be at least 5 µl, preferably in a range of 20 to 100 µl. If the amount of the reaction mixture drop is smaller than 5 µl, reproducibility of data or accuracy is not sufficiently satisfactory. The upper limit is to save blood collection or an amount of a sample to be assayed.

The B/F separating layer is prepared to function in accordance with a variety of separation methods as described below.

In general, the B/F separating layer passes a substance having a smaller shape or molecular weight (usually, F is an antigen or antibody labelled with a spectral sensitizer(s) which has ordinarily a size of approximately 2-3 Å to 500-600 Å in a diameter, though the size depends upon, of course, the kind of immunologically active substances to be assayed, whereas B usually has a diameter of at least 100 Å though it is likewise difficult to set forth its range generally) therethrough to allow the passed substance to reach the silver halide photosensitive layer. This type of B/F separation is most typical and practical. However, when utilizing a molecular filter or, in the case of adsorption type separation, utilizing ionic adsorption or physical adsorption, B/F separation occurs depending upon the principle used in such separation methods; typical examples of B/F separation methods are described, together with principles for separation, in *SEIKAGAKU DATA BOOK (BIOCHEMICAL DATA BOOK)*, a second separate volume, Chapter 10, published by Tokyo kagaku Dojin (1980).

B/F separating materials employed for B/F separation layers in the multilayer analysis sheet can also be extended to B/F separating materials typically employed for RIA, etc. Specific examples of B/F separating materials are as follows.

(1) Materials generally called filtering materials or filters or so-called permeable membranes, i.e., filter paper, microfilter, etc.

(2) Hydrophilic synthetic high molecular weight substances (e.g., polyethylene glycol, polyvinyl alcohol, polyhydroxyethyl acrylate, polyethylene oxide, polyacrylamide, etc.) or hydrophilic natural high molecular weight substances (e.g., hydroxyethyl cellulose, carboxymethyl cellulose, carboxyethyl cellulose, gum arabic, agar, gelatin, etc.) having dispersed therein adsorbents (e.g., carbon black, talc, an ion exchange resin, floridyl, cellulose powders, dextran-carbon powders, Sephadex, etc.). In this case, hydrophilic synthetic or natural high molecular weight substances can also be used singly without dispersing therein any adsorbent. Further, hydrophilic synthetic high molecular weight substances can also be used in combination with natural high molecular weight substances.

(3) So-called fiber cloth, i.e., cotton, hemp, silk, rayon, polyesters, nylon, etc.

Where filtering materials or filters in (1), or fiber cloth in (3) are employed, precipitated solid B is separated by filteration.

Where hydrophilic synthetic high molecular weight substances or natural high molecular weight substances are employed singly or in combination, without using any adsorbent, B/F separation occurs through molecular filtering depending upon the size of the net structure in the layer formed by these molecular chains. In the case where non-adsorbent polymers (Sephadex, etc.) are incorporated in the net structure, the same type of separation occurs.

In the case where these high molecular weight substances form a layer having an anionic or cationic group(s) or having incorporated in the net structure an ionic adsorbent such as ion exchange resins, the B/F separating material provides a layer to which a separation method utilizing difference in ionic adsorption of B and F is applicable.

Further, in case where these high molecular weight substances possess hydrophobic groups as a part of the molecules or possess adsorbents such as active charcoal in the net structure, the B/F separating material can form a layer to which a separation method utilizing differences in physical adsorption of B and F is applicable.

The B/F separating layer provided in the analysis sheet can be composed of two or more layers in order to improve the effect of separating a specimen to be assayed, i.e., B and F.

Where a filter paper, a microfilter, a millipore filter, etc., are employed as B/F separating materials, it is necessary to choose materials having an adequate pore size depending upon the components to be assayed, but it is generally preferred to have a pore size of 1 to $10^5$ Å, more preferably 10 to $10^3$ Å.

The thickness of the B/F separating layer provided in the multilayer analysis sheet should adequately be determined depending upon the components to be assayed, B/F separating materials used, etc., however, it is generally preferred that the thickness be in a range of 0.1 to 500 microns, more preferably in a range of 0.5 to 300 microns.

When high molecular weight substances are employed in combination with adsorbents, it is necessary to suitably determine the ratio of the high molecular weight substances to adsorbents, depending upon materials used. In general, however, it is preferred that the ratio (by weight) be in a range of 20/80 to 99/1, more preferably 99/5 to 60/40.

The addition of inorganic salts such as ammonium sulfate, sodium chloride, etc. to the B/F separating materials shown in (1) to (3) above, especially to polyvinyl alcohol, gelatin, etc., provides improved B/F separation effect. The addition amount of the inorganic salts is not overly limited; however, it is generally in a range of about 1:1 to about 100:1 (by weight ratio) in a B/F separating material/inorganic salt ratio.

In the present invention, a labelled antigen or antibody (F) is separated from a labelled antigen-antibody bound product (B) in a very simple manner using the multilayer analysis sheet. From a practical viewpoint, it is advantageous that an antigen-antibody reaction is caused utilizing a double antibody (a second antibody method) and the supernatant which is inherently separated from the precipitate but not completely pure is taken out and dropwise added to the multilayer sheet. This procedure saves a time consuming centrifugal separation step which is unavoidable in conventional B/F separation.

The B/F separating layer is provided on a support by, e.g., coating a B/F separating material, laminating it, immersing a support in it, spraying it, etc., which is suitably chosen depending upon the B/F separating material used.

More specifically, the B/F separating layer provided in the analysis sheet of this invention can be provided, in the case of using a microfilter, millipore filter, a filter paper, etc., as B/F separating agents, by laminating these agents onto a silver halide layer. In case of using Sephadex, an ion exchange resin, polyethylene glycol, etc., B/F separating materials are dissolved or dispersed in solvents such as water, methanol, methylene chloride, ethyl acetate, butyl acetate, acetone, etc., and the resulting solution is coated onto a silver halide layer to thereby provide a B/F separating layer.

Upon coating, coating aids can be employed, for example, nonionic surface active agents such as saponin (steroid type), polyalkylene glycol alkylamines or amides, polyethylene oxide adducts of silicone, glycidol derivatives (e.g., alkenylsuccinic acid polyglycerides, alkylphenol polyglycerides), fatty acid esters of polyvalent alcohols, alkyl esters of sugars, urethanes of sugars, ethers of sugars, etc.; anionic surface active agents containing acidic groups such as a carboxy, sulfo, phospho, sulfate radical, phosphate radical, etc., e.g., triterpenoid type saponin, alkyl carbonates, alkyl sulfonates, alkylbenzene sulfonates, alkylnaphthalene sulfonates, alkyl phosphates, alkyl sulfates, N-acyl-N-alkyl taurines, sulfosuccinates, sulfoalkyl polyoxyethylene alkyl phenyl ethers, polyoxyethylene alkyl phosphates, etc.; amphoteric surface active agents such as amino acids, aminoalkyl sulfonic acids, aminoalkyl sulfonates or phosphates, alkyl betaines, amineimides, amine oxides, etc.; cationic surface active agents alkyl amine salts, aliphtatic or aromatic tertiary ammonium salts, heterocyclic tertiary ammonium salts such as pyridinium, imidazolium, etc., or phosphonium or sulfonium salts containing an aliphatic or heterocyclic ring.

Specific examples of these surface active agents are those described in U.S. Pat. Nos. 2,240,472, 2,831,766, 3,158,484, 3,210,191, 3,294,540, and 3,507,660, British Pat. Nos. 1,012,495, 1,179,290 and 1,198,450, Japanese patent application Laid Open OPI No. 117,414/75, U.S. Pat. Nos. 2,739,891, 2,823,123, 3,068,101, 3,415,649, 3,666,478 and 3,756,828, British Pat. 1,397,218, U.S. Pats. 3,133,816, 3,441,413, 3,475,174, 3,545,974, 3,726,683 and 3,843,368, Belgian Pat. 731,126, British Pat. Nos. 1,138,514, 1,159,825 and 1,374,780, Japanese Patent Publications Nos. 378/65, 379/65 and 13822/68, U.S. Pat. Nos. 2,288,226, 2,944,900, 3,253,919, 3,671,247, 3,772,021, 3,589,906, 3,666,478 and 3,754,924, German patent application OLS No. 1,961,638, Japanese Patent Application Laid Open OPI No. 59025/75, etc.

The silver halide layer contained in the multilayer type analysis sheet of this invention refers to a layer comprising silver halide. Specific examples of silver halide include silver chloride, silver chlorobromide, silver bromide, silver iodobromide, silver chloroiodobromide, silver chloroiodide, silver iodide, etc.

Further, the silver halide layer can also be a so-called emulsion comprising a hydrophilic binder having dispersed or suspended therein silver halide, or can also be silver halide provided on a support, without any binder, e.g., by providing a silver halide layer by means of a vacuum evaporation, sputtering, etc.

Furthermore, the silver halide layer in this invention can be a single layer or, if necessary, can be composed of two or more layers. It is sufficient for purpose of assay that the thickness of the silver halide layer be set forth so as to have an optical density of 6.0 at greatest.

Silver halide(s) contained in a photographic emulsion used in the present invention include those described in Ser. Nos. 126,919 and 126,920 filed Mar. 3, 1980 and can be prepared in a conventional manner, e.g., by a single jet method, a double jet method, or a combination thereof. Useful preparation methods of silver halide emulsions are described in, e.g., Trivelli and Smith, *The Photographic Journal*, vol. 79, pp. 330–338 (1939), C. E. K. Mees, *The Theory of the Photographic Process*, published by Macmillan, Glafkides, *Photographic Chemistry*, vol. I, pp. 327–336, published by Fountain Press, etc.

Silver halide emulsions employed in the multilayer analysis sheet of the present invention can contain conventional photographic addenda, if desired, i.e., various sensitizers, anti-foggants, stabilizers, coating aids, antistatic agents, plasticizers, fluorescent whitening agents, developing accelerating agents, color toning agents, etc. In addition, silver halide emulsions can also contain various color image forming couplers, i.e., aromatic amines (normally primary amines), compounds capable of forming dyes by the reaction with the oxidation products of developing agents, organic solvents, etc., as is shown in Ser. Nos. 126,919 and 126,920.

As the silver halide emulsion(s) used in this invention, gelatino silver halide emulsions are generally employed but this is not mandatory. For example, instead of gelatin, substances that do not adversely affect light sensitive silver halides such as albumin, agar, gum arabic, alginic acid, acylated gelatin (e.g., phthalated gelatin, malonated gelatin, etc.), hydrophilic polymers such as polyvinyl alcohol, polyvinyl pyrrolidone, polyacrylamide, polystyrene sulfonic acid, cellulose compounds (e.g., hydroxyethyl cellulose, carboxymethyl cellulose, dextrin, etc.), water-soluble starch, etc., can be used. Further, combinations thereof can be used.

Methods for providing silver halide emulsion layer(s) in the multilayer analysis sheet of the present invention are conventional in photographic light sensitive material art, details of which are described in *Coating Technology*, published by Asakura Publishing Co. (1973), etc.

For coating silver halide emulsion(s), etc., a dip coating method, a roller coating method, a curtain coating method, an extrusion coating method, etc. can be used.

As supports employed in the multilayer analysis sheet of this invention, flexible supports such as a plastic film, paper, cloth, etc., or rigid supports such as glass, porcelain, metal, etc., can be used. Useful plastic supports are films comprising semi-synthetic or synthetic high molecular weight substances such as cellulose nitrate, cellulose acetate, cellulose acetate butyrate, polystyrene, polyvinyl chloride, polyethylene terephthalate, polycarbonate, etc.; a paper sheet having coated thereon a baryta layer or alpha-olefin polymers (e.g., polyethylene polypropylene, ethylene/butene copolymer, etc.).

The surface of the supports can also be subjected to a subbing treatment to effect adhesion to a silver halide emulsion layer(s). The support surface can also be subjected to a corona discharge treatment, a UV irradiation treatment, a flame treatment, etc.

In addition to the B/F separating layer, a support and a silver halide emulsion layer(s), intermediate layer(s) can be provided in the multilayer analysis sheet of this invention, if necessary, and an intermediate layer(s) can be provided to achieve complete adhesion in respective layers, protection of these layers, etc.

As processing solutions employed in development processing in this invention, known processing solutions are typically employed. The processing temperature is generally between 18° and 50° C., but can be lower than 18° C. or higher than 50° C. Depending upon the purpose, any development processing for forming silver images (black-and-white photographic processing) or color photographic processing comprising development processing to form color images can be used.

Development processing performed in this invention is conventional. For example, where emulsions are coated onto a support, development can be carried out in accordance with methods conventionally used for photographic development. More specifically, methods of development processing conventional to photographic films or printing paper, etc., can be employed. For example:

(1) color development→stop→bleach→wash→fix→wash→stabilization—dry;

In this processing, a pre-bath, a hardening bath, etc., may be employed before the color development and also a stabilization or wash after bleach may be omitted.

(2) black-and-white development→stop→fix→wash→stabilization→dry;

(3) black-and-white development→stop→wash→fogging→wash→color development→stop→wash→bleach→wash→fix→wash stabilization→dry;

These processing are illustratively indicated merely for development processing. Baths used in these processings can be the same or different.

Developing solutions having the compositions as indicated in the examples hereinafter are typically used in the above processings.

Typical examples of fixing solutions and bleaching solutions are those having compositions conventional in the art and are shown in Ser. Nos. 126,919 and 126,920.

In addition to the foregoing, various modifications in processings, processing solutions, additives and the like are described in Ser. Nos. 126,919 and 126,920 in detail. In this regard, the disclosures in Mason, *Photographic Processing Chemistry*, pp. 163–165, *Research Disclosure* No. 169 RD-16928, *Journal of the Society of Motion Picture and Television Engineers*, vol. 61, pp. 667–701(1953), U.S. Pat. Nos. 2,193,015 and 2,592,364 are hereby incorporated by reference.

In addition, development and other photographic processing can also be carried out by extruding onto, coating onto, immersing in or spraying onto a support having coated thereon an emulsion various photographic processing agents. Further, where an emulsion is in the liquid state, photographic processing can be performed by adding to and mixing with the liquid emulsion the desired photographic agents.

Trace components which can be detected and/or measured by the method of this invention typically include trace components in the living body, but drugs, in addition thereto, can also be detected and/or measured.

Specific examples of such trace components include peptide hormones (e.g., insulin, glucagon, parathyroid hormone, carcitonin, erythropoetin, secretin, cholecystokinin, gastrin, angiotensin II, vasopressin, oxytocin, melanin cell-stimulating hormone, adrenal cortex stimulating hormone, thyroid stimulating hormone, growth hormone, prolactin, corpus luteum stimulating hormone, follicle stimulating hormone, etc.); non-peptide hormones (e.g., steroid hormones such as glucocorticoid, aldosterone, adrenergic androgene, estrogene, progesterone, testosterone, etc.); other hormones such as thyroid hormones (e.g., thyroxin, triiodothyronine, etc.), cortisol, estriol, adrenalin, noradrenalin, melatonin, acetylcholine; enzymes such as $C_1$ esterase, alkali phosphatase, pepsinogen, trypsin; kinase virus; specific antigens; tumor antigens (e.g., alpha-fetoprotein),; blood serum protein components (e.g., human lysozyme, thyroxin-bound globulin, IgG, IgE, etc.); drugs (e.g., LSD, etc.) and others (e.g., rheumatoid factor, myosin, etc.).

Spectral sensitizers employed for labelling in this invention are well known as spectral sensitizers for photographic light sensitive materials. Cyanine dyes, merocyanine dyes, hemicyanine dyes, styryl dyes, etc. are representative thereof. Detailed disclosure of such spectral sensitizers is provided in *The Theory of the Photographic Process*, fourth edition, edited by T. H. James, 1977, published by MacMillan Co., Ltd., *Cyanine Dyes and Related Compounds*, F. M. Hamer, 1964, Interscience Publishers, etc. Exemplary of specific dyes useful in this invention are merocyanine dyes as described in U.S. Pat. Nos. 2,493,748, 2,519,001 and 2,652,330; West German Patent 1,177,841; French Pat. No. 1,412,702; British Pat. No. 489,335, etc.; cyanine dyes as described in U.S. Pat. Nos. 2,238,213, 2,503,776, 2,537,880, 3,196,017 and 3,397,060; West German Pat. Nos. 929,808, 1,028,718, 1,113,873, 1,163,671 and 1,177,482; French Pat. 1,359,683; British Pat. Nos. 840,223, 886,270, 886,271 and 904,332; Belgian Pat. No. 654,816; Japanese Patent Publications 14112/65 and 23467/65, etc. These dyes can also be employed as a combination of two or more thereof. Supersenstization, including the use of the aforesaid dyes in combination with dyes as described in, e.g., Japanese Patent Publications Nos. 4932/68, 4936/68 and 22884/68 is also useful in this invention. Further, supersensitization as described in U.S. Pat. Nos. 2,947,630, 2,933,390, 2,937,089, 3,617,295 and 3,635,721 and French Pat. No. 1,500,218, etc., is also useful. Supersensitizers can be mixed together with the labelled antigen or antibody or can be previously incorporated into a silver halide emulsion.

Of these spectral sensitizers, sensitizers containing an amino, imino, mercapto, carboxy, amido or hydroxy group(s) therein are particularly preferred from the aspect of smooth labelling reaction.

As described above, spectral sensitizers having an absorption region longer than intrinsic absorption wavelength region of silver halide are used in this invention. This is because it is necessary that silver halide latent images formed by intrinsic absorption of silver halide per se be differentiated from silver halide latent images formed by light absorption of the spectral sensitizers; the latter images are measured as a black density which permits one to determine an unknown amount of a substance to be analyzed.

A method for labelling an antigen or antibody with a spectral sensitizing dye(s) (or a spectral sensitizer(s); these terms are interchangeably used in this invention) for photographic use involves chemical reaction, i.e., the spectral sensitizing dye(s) are reacted with an antigen or antibody through a covalent bond(s) to form a labelled reaction product. Reaction occurs between the spectral sensitizer(s) and functional groups contained in the antigen or antibody, e.g., an amino, imino, mercapto, carboxy, carbonamido, hydroxy, etc., group. The method of bond formation between both can be any of the following:

(1) Spectral sensitizers are directly reacted with the aforesaid functional groups;

(2) Spectral sensitizers and the aforesaid functional groups are reacted using an activating agent, and (3) Spectral sensitizers and the aforesaid functional groups are reacted through a compound having a bi-functional group.

In these reactions, it is important that reaction conditions be chosen so as not to inhibit biological activities of the antigen or antibody to be labelled. Details of reaction conditions are described in Ser. No. 126,920 filed Mar. 3, 1980. These reaction conditions are generally common to those available for chemical modification of proteins and enzymes and are described in, e.g., *PROTEIN, NUCLEIC ACID & ENZYME*, 10, 1127 (1970), entitled "Chemical Modification of Enzyme and Protein—List of Publications for Respective Amino Acid Residues" by Soji Rokushika et al, and *SEIKAGAKU JIKKEN KOZA* (Lecture on Biochemical Experiment) I, 4th separate volume, 10–203 (1977) edited by Nihon Kagakukai, published by Tokyo Kagaku Dojin Publishing Co.

Antigen or antibody materials containing reactive groups which provide bond formation as above described and the reactions thereof are described in detail in *SEIKAGAKU JIKKEN KOZA* (Lectures on Biochemical Experiment) 1, entitled: Chemistry of Protein" edited by Nihon Seikagakukai, published by Tokyo Kagaku Dojin Publishing Co. (1977); Izumiya, *PEPTIDE GOSEI* (Synthesis of Peptides), etc. One skilled in the art can easily perform such reactions for forming bonds from knowledge in the art and these publications.

Compounds containing functional groups that react with the aforesaid functional groups include:

alkyl chloroformates, aldehydes, isocyanates, vinyl compounds, active halogens, imidazoleamides, pyridinium compounds, sulfonic acid esters, bismaleimides, diazonium compounds, epoxy compounds, acid anhydrides, carboxylic acids, ethyleneimines, active esters, acid halides, amines, alkyl halides, nitrophenyl halides, and the like, details of which are described in Ser. No. 126,920 filed Mar. 3, 1980.

These functional groups can inherently be present in the spectral sensitizers or can be introduced into the spectral sensitizers via chemical reaction(s) such as an addition reaction, a substitution reaction, a Schiff's base formation reaction, etc., directly or using compounds having these functional groups.

The amount of spectral sensitizer(s) used for labelling an antigen or antibody varies depending upon kind of the antigen or antibody, but such is generally used in a molar ratio of 1 to 700 times that of the antigen or antibody, preferably 1 to 100 times, same basis.

Simple tests are sufficient to confirm completion of labelling. Where it is confirmed utilizing absorption spectrum, following completion of the labelling reaction, the absorption spectrum of a separated and purified product is measured; if the resulting absorption spectrum is consistent with the intrinsic absorption spectrum which the spectral sensitizer possesses, also considering association when using a solvent(s), it is confirmed that the labelling reaction is effected. A further method for confirming the labelling is to analyze the presence or absence of a specific terminal group(s), e.g., an amino or carboxy groups(s). In the case that the spectral sensitizer is introduced at the terminal amino group(s) thereof, it is confirmed by the analysis of the N-terminal that the labelling reaction has been completed if the corresponding amino acid(s) on which labelling is to be caused are not detectable. In a similar manner, the terminal carboxy group(s) are analyzed to check completion of the labelling reaction, details of which are described in B. S. Hartley et al. *Biochim. Biophys. Acta*, 21, 58 (1956), *Archn. Biochem. Biophys.*, 22, 475 (1949), *Biochem. J.*, 39, 507 (1945), *Bull. Chem. Soc. Japan*, 25, 214 (1952), *Biochem. Biophys. Res. Communication*, 22, 69 (1966), etc. Further, details of these terminal determination methods are also given as a review in S. B. Needleman, *PROTEIN SEQUENCE DETERMINATION*, published by Springer Verlag (Berlin), 1975.

In the method for immunological assay using a fogging agent or agents as a labelling substance(s), these substances are known as chemical sensitizers for photography and typically include sulfur-containing compounds, reducible compounds, metal complexes, etc. Details of useful fogging agents are given in, e.g., *The Theory of the Photographic Process*, 4th edition, edited by T. H. James, pp. 393–395, 1977, MacMillan Publishing Co. Specific examples of these fogging agents are described in Ser. No. 126,919, supra.

Various light sources can be employed for exposing the silver halide(s) brought into contact with the labelled compound, in photochemical immunological assay in which a spectral sensitizer(s) for photographic use are employed as a labelling compound(s). For exposure, the light has wavelengths that the spectral sensitizers alone absorb; other light having a wavelength in the absorption region intrinsic to silver halide is filtered out. As suitable exposure degree is generally from $10^1$ to $10^{10}$ cms.

As light sources, for example, a tungsten lamp, a halogen lamp, a mercury lamp, a xenon lamp, etc., can be employed in combination with a suitable optical filter (e.g., a sharp cut filter manufactured by Fuji Photo Film Co., Ltd., a metal interference filter, etc.). In addition, a solid laser (e.g., a ruby laser), a semiconductor laser (e.g., a lead sulfide laser), a dye laser, a gas laser (e.g., a neon helium laser, an argon laser), etc. can be advantageously employed.

In the present invention, a film-like laminate type analysis sheet is employed for immunological and photochemical assay. Therefore, effects that are not seen in conventional immunological assay can be found.

The main effect achieved by this invention resides in that a layer(s) having other functions can be introduced into the analysis sheet of this invention since a film-like analysis sheet comprising silver halide is utilized. More specifically, a long period of time is required in a conventional assay method because a centrifuge is needed in B/F separation. However, time can be shortened by providing the B/F separation layer so that procedures can be simplified.

The effect of this invention also resides in eliminating any danger to the human as in the use of radioisotopes, and thus reducing equipment cost. According to this invention, drawbacks such as radioisotope-labelled substance which are unstable due to radioactive decay are eliminated so that analytical data of high reproducibility is always obtained.

Though the multilayer analysis sheet is similar in its construction to conventional silver halide photographic elements, a major difference lies in that the latter involves a hardening treatment necessarily required for protecting a silver halide layer(s) upon processing, gelatin thereby being randomly cross-linked (pore size distribution is wide and non-uniform); with such multilayer elements, B/F separation occurs only with extreme difficulty. In order to effect B/F separation, hardening has adverse effects. Thus, in the multilayer analysis sheet, no hardening is performed.

This invention will be described in detail below with reference to the examples.

EXAMPLE 1

In 10 ml. of a 0.01 M tris hydrochloride buffer solution, 5 mg. of insulin was dissolved. To the resulting solution, 5 mg. of 3,3'-dicarboxymethyl-meso-bromonaphthothiadicarbocyanine chloride and 1 μl of isobutyl chloroformate and then 1 μl of triethyl amine were added. Further, 1 mg. of N-hydroxysuccinimide were added thereto. The mixture was allowed to react at −15° C. for about 15 mins. and then at 0° C. for 24 hrs. to effect labelling of insulin with the sensitizing dye. The reaction mixture was subjected to a gel filtration method, i.e., desalted with Sephadex G-25, equilibrated with 1 M acetic acid, to obtain a sensitizing dye-labelled insulin fraction. The product further purified with DEAE cellulose was used as a labelled substance, i.e., labelled insulin.

Next, antigen-antibody reaction was carried out using the thus labelled insulin and antibody, i.e., guinea pig anti-insulin serum. That is, Components (1), (2), (3) and (4) indicated below were mixed, respectively and the mixture was allowed to stand at 4° C. for 48 hrs., whereby seven(7) insulin solutions (Component 1) where the insulin concentration was varied as indicated below were produced.

| | | |
|---|---|---|
| (1) | Insulin (with varied concentrations) (0 μU, 20 μU, 40 μU, 80 μU, 160 μU, 320 μU and 640 μU) | 100 μl |
| (2) | Borate buffer solution (0.5% BSA) | 100 μl |
| (3) | Labelled insulin | 100 μl |
| (4) | Guinea pig anti-insulin serum (1/25000) | 100 μl |

Further, a solution containing a second antibody having the following composition was added in a fixed amount to the thus obtained reaction mixtures having seven(7) different concentrations of insulin, respectively. The resulting mixture was allowed to stand for 24 hrs. at 4° C.

| | |
|---|---|
| Normal guinea pig serum (1/200) | 50 μl |
| Rabbit anti-guinea pig gamma-globulin serum (1/5) | 150 μl |

On the other hand, an AgBrCl emulsion (Cl⁻ content 20 mol%, average grain size 0.8μ) which was unexposed and spectrally unsensitized was prepared in a conventional manner and then coated onto a triacetate cellulose base (thickness 140 microns). Polyacrylamide was further coated thereon in a thickness of 0.5μ, followed by drying. Thus, a multilayer analysis sheet as shown in FIG. 1 was prepared.

Onto the thus prepared multilayer analysis sheet, 25 μl of the supernatants of the reaction mixtures was dropped, respectively, which was allowed to stand for 20 mins. at 20° C. Thereafter, each of the sheets was exposed to light through a SC-60 filter (tradename, made by Fuji Photo Film Co., Ltd.) at 60 Lux for 300 secs. and then developed at 20° C. for 5 mins. with Developer A having the following composition.

| Developer A: | |
|---|---|
| Metol | 0.31 g |
| Sodium hydrogen sulfite | 39.6 g |
| Hydroquinone | 6.0 g |
| Sodium carbonate (monohydrate) | 21.9 g |
| Potassium bromide | 0.86 g |
| Citric acid | 0.68 g |
| Potassium metabisulfite | 1.50 g |
| Water to make 1 liter | |

After fixing, washing with water and drying in a conventional manner, the optical density of each of the photographic films was measured with a densitometer made by Fuji Photo Film Co., Ltd. to prepare a calibration curve.

Next, the same procedure was conducted using 100 μl of a test sample containing an unknown concentration of insulin. Compared the optical density thus measured with the calibration curve, the unknown concentration of insulin was determined.

EXAMPLE 2

In Example 1, a mixture of cellulose powders and hydroxyethyl cellulose (30/70 by weight ratio) was used as a B/F separation layer instead of polyacrylamide. By coating the mixture as in Example 1, a laminate analysis sheet having a B/F separation layer of a 1.5μ thickness was prepared.

Next, after labelled insulin was prepared in a manner similar to Example 1, antigen-antibody reaction was conducted similarly except that 300 μl of ethanol was used at the second step, antigen-antibody reaction, instead of rabbit anti-guinea pig gamma-globulin serum or the second antibody.

The thus obtained supernatant liquids of the reaction solutions were taken up by 28 μl each and dropped onto the analysis sheet. The system was allowed to stand for 20 mins. at 20° C. The multilayer analysis sheet was processed in a manner similar to Example 1 to prepare a calibration curve from the thus obtained optical densities.

Then, the same procedure was repeated using 100 μl of a test sample containing an unknown concentration of insulin. By comparing the optical density of the test sample with the calibration curve, the unknown concentration of insulin was determined.

EXAMPLE 3

Procedures similar to Example 1 were carried out to label hGH except that 1-carboxymethyl-1'-ethyl-4,2'-quinocarbocyanine iodide (spectral sensitizer) was used as a labelling substance.

Using the thus obtained labelled hGH and hGH standard references having various known concentrations, antigen-antibody reaction was conducted. That is, Components (1) through (4) indicated below were thoroughly mixed in a test tube and the resulting mixture was incubated at 4° C. for 48 hrs.

| | | |
|---|---|---|
| (1) | Standard hGH reference (with varied concentrations) (80, 40, 20, 10, 5, 2.5, 1.25, 0.62 and 0 ng/ml) | 0.1 ml |
| (2) | Buffer solution (0.05M Vevonal Buffer, pH 8.6, containing 0.5% BSA) | 0.4 ml |
| (3) | Labelled hGH | 0.1 ml |
| (4) | Anti-hGH guinea pig serum | 0.1 ml |

To each of 9 kinds of the thus reacted mixtures (primary reaction), 0.1 ml. of anti-guinea pig gamma-globulin goat serum was added as a second antibody, respectively. The resulting mixture was thoroughly mixed followed by incubation at 4° C. for 24 hrs.

On the other hand, an AgBrI emulsion (I content 5 mol%, average grain size 0.7μ), which was either unexposed or spectrally unsensitized was prepared in a conventional manner and then coated in a thickness of 2 microns onto a polyethylene terephthalate sheet having a thickness of 200 microns. Further thereon, polyhydroxyethyl acrylate was coated in a thickness of 1 micron. After drying at room temperature for 48 hrs., a multilayer analysis sheet was prepared.

Onto the thus prepared multilayer analysis sheet, the above reaction mixtures were dropwise added by 30 μl each. Thereafter, exposure and development were conducted in a manner similar to Example 1 and the resulting optical densities were measured to give a calibration curve.

Next, the same procedure was conducted using a test sample containing an unknown concentration of hGH. By comparing with the calibration curve, the unknown concentration of hGH was determined.

EXAMPLE 4

In the multilayer analysis sheet obtained in accordance with Example 3, a microfilter capable of permeating high molecular weight substances having a molecular weight of 50,000 was laminated on the silver halide layer instead of the polyhydroxyethyl acrylate layer to give a multilayer analysis sheet. The thus prepared B/F separation layer possessed a thickness of 200 microns and a pore size of 100 A.

Immune analysis was conducted in a manner similar to Example 3 except that the above obtained analysis sheet was employed and after the reaction mixture was dropwise added to the analysis sheet, the B/F separation layer was stripped off followed by exposure and development.

EXAMPLE 5

An AgBrI emulsion (I content, 5 mol%; average grain size 0.7μ) which was either unexposed or spectrally unsensitized was prepared in a conventional manner. Thereafter, the emulsion was coated in a thickness of 2μ onto a polyethylene terephthalate base having a thickness of 200 microns. Further, a cloth of cotton No. ? was laminated on the silver halide layer to prepare a laminate analysis sheet.

Onto the thus prepared analysis sheet, the reaction mixtures obtained in accordance with Example 3 were dropwise added by 30 μl each, which was then allowed to stand. After the cloth was stripped off, exposure and development similar to Example 1 were conducted. The resulting optical densities were measured to give a calibration curve.

Next, the same procedure was repeated as in Example 3 except that a test sample containing an unknown concentration of hGH was used. By comparing with the calibration curve, the unknown concentration of hGH was determined.

While the invention has been described in detail and with reference to specific embodiments thereof, it will be apparent to one skilled in the art that various changes and modifications can be made therein without departing from the spirit and scope thereof.

What is claimed is:

1. A method of performing a competitive immunoassay for a trace component in a sample comprising:
    (a) adding a labelled antigen or labelled antibody to said sample in a competitive immunoassay protocol, said label being selected from the group consisting of a spectral sensitizer and a fogging agent,
    (b) permitting the immune reactions to take place,
    (c) contacting the resulting reaction mixture with a multilayer analysis sheet comprising a support having provided thereon, in sequence, (1) a silver halide light sensitive layer and (2) a free labelled immunochemical/bound labelled immunochemical separating layer,
    (d) contacting either the free labelled immunochemical or the bound immunochemical which has passed through said separating layer with said silver halide light sensitive layer, said immunochemical being either antigen or antibody,
    (e) when said label is said spectral sensitizer, exposing the resultant product of step (d) to light having a wavelength which the spectral sensitizer label absorbs,
    (f) developing the multilayer analysis sheet; and
    (g) measuring the optical density resulting from step (f).

2. The method of claim 1 wherein said silver halide layer does not contain any spectral sensitizer.

3. The method of claim 1 wherein a thickness of said free labelled immunochemical/bound labelled immunochemical separating layer is in a range of 0.1 to 500 microns.

4. The method of claim 1 wherein said free labelled immunochemical/bound labelled immunochemical separating layer is composed of a filter material, a filter or a permeable membrane, having a pore size of about 1 Å to about $10^5$ Å.

5. The method of claim 1 wherein said free labelled immunochemical/bound labelled immunochemical separating layer comprises at least a dispersion of an adsorbent in a hydrophilic, synthetic, high molecular weight substance or a natural, high molecular weight substance.

6. The method of claim 1 wherein said free labelled immunochemical/bound labelled immunochemical separating layer is composed of a natural, high molecular weight substance or a hydrophilic, synthetic, high molecular weight substance.

7. The method of claim 1 wherein said free labelled immunochemical/bound labelled immunochemical separating layer is composed of a fiber cloth.

8. The method of claim 1 wherein said labelling substance is a spectral sensitizer.

9. The method of claim 1 wherein said labelling substance is a fogging agent.

* * * * *